(12) United States Patent
Lemann et al.

(10) Patent No.: US 6,589,538 B1
(45) Date of Patent: *Jul. 8, 2003

(54) ANHYDROUS COMPOSITION AND COSMETIC, PHARMACEUTICAL OR HYGIENIC USE

(75) Inventors: Patricia Lemann, Creteil (FR); Annick Collette, Choisy le Roi (FR); Isabelle Bara, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/344,104

(22) Filed: Jun. 24, 1999

(30) Foreign Application Priority Data

Jun. 25, 1998 (FR) .......................................... 98 08086

(51) Int. Cl.[7] .......................... A61K 7/021; A61K 7/05; A61K 7/32; A61K 7/06; A61K 7/11
(52) U.S. Cl. .......................... 424/401; 424/63; 424/64; 424/65; 424/70.1; 424/70.12
(58) Field of Search .......................... 424/401, 63, 64, 424/65, 70.1, 70.12

(56) References Cited

U.S. PATENT DOCUMENTS

| | | | |
|---|---|---|---|
| 3,439,088 A | | 4/1969 | Edman |
| 3,818,105 A | | 6/1974 | Coopersmith et al. |
| 4,973,476 A | * | 11/1990 | Krzysik .......................... 424/71 |
| 5,034,216 A | * | 7/1991 | Barone et al. .......................... 424/63 |
| 5,298,236 A | * | 3/1994 | Orr et al. .......................... 424/47 |
| 5,470,563 A | * | 11/1995 | Tanaka et al. .......................... 424/448 |
| 5,562,978 A | * | 10/1996 | Jacobson .......................... 428/323 |
| 5,567,426 A | * | 10/1996 | Nadaud et al. .......................... 424/401 |
| 5,620,980 A | * | 4/1997 | Samour .......................... 514/256 |
| 5,650,139 A | * | 7/1997 | Nojima .......................... 424/64 |
| 5,725,845 A | | 3/1998 | Krog et al. |
| 5,744,130 A | * | 4/1998 | Guskey et al. .......................... 424/66 |
| 5,849,316 A | | 12/1998 | Mellul et al. |
| 5,885,559 A | * | 3/1999 | Lee et al. .......................... 424/65 |
| 5,925,338 A | * | 7/1999 | Karassik et al. .......................... 424/65 |

FOREIGN PATENT DOCUMENTS

| | | |
|---|---|---|
| CA | 2 223 742 | 6/1998 |
| EP | 0 266 921 | 5/1988 |
| EP | 0 548 694 | 6/1993 |
| EP | 0 704 205 | 4/1996 |
| EP | 0 756 864 | 2/1997 |
| GB | 2 294 392 | 5/1996 |
| JP | 1-143812 | 6/1989 |
| WO | WO 97/16157 | 5/1997 |

OTHER PUBLICATIONS

English language Derwent Abstract of CA 2 223 742, Jun. 1998.
English language Derwent Abstract of EP 0 756 864, Feb. 1997.
Derwent Publication, Ltd., London, AN 89–204063, JP 01 143812, Jun. 6, 1989.

* cited by examiner

Primary Examiner—Jose' G. Dees
Assistant Examiner—Marina Lamm
(74) Attorney, Agent, or Firm—Finnegan, Henderson, Farabow, Garrett & Dunner, L.L.P.

(57) ABSTRACT

The subject-matter of the present invention is a stable anhydrous composition for cosmetic or pharmaceutical use comprising at least one volatile solvent and at least one pigment, wherein said composition further comprises at least one oxyalkylenated silicone substituted at the $\alpha$ and $\omega$ positions.

68 Claims, No Drawings

ANHYDROUS COMPOSITION AND COSMETIC, PHARMACEUTICAL OR HYGIENIC USE

The subject-matter of the present invention is anhydrous cosmetic compositions for cosmetic or pharmaceutical use.

Make-up compositions comprising a fatty phase are commonly used in cosmetics because of their good adhesion to the epidermis, their feeling of comfort, their protective capability and their ability to form a water-impermeable film. Anhydrous make-up products are generally provided in the form of a compact solid or else in the form of a cream. They can also be provided in the form of a fluid gel.

These compositions can constitute products for caring for the skin, including the scalp, and/or products for making up the skin, mucous membranes (lips or interior of the eyelids), semimucous membranes (lips) or keratinous fibres (hair, eyelashes, nails), or products for making up the body.

However, those skilled in the art still seek to improve the stability of products of this type.

Furthermore, these compositions, when they are applied to the skin, mucous membranes or semimucous membranes, can exhibit the disadvantage of transferring. This is understood to mean that the composition is capable of being deposited, at least partly, on certain substrates with which it is brought into contact, such as, for example, a glass, an item of clothing or the skin.

On being deposited, the said composition leaves a mark on the said substrate. The result of this is therefore a mediocre persistence of the composition on the skin or mucous membranes, resulting in the need to regularly renew its application.

Furthermore, the appearance of unacceptable marks on certain items of clothing and in particular on blouse collars can dissuade some people from using this type of make-up.

Another disadvantage of these compositions can reside in the problem of migration. This is because it has been found that some compositions had a tendency to spread inside the fine lines and/or wrinkles of the skin, in the case of foundations; into the fine lines which surround the lips, in the case of lipsticks; or into the folds of the eyelid, in the case of eyeshadows. In the case in particular of eyeshadows, the appearance of streaks in the make-up, generated by the movements of the eyelids, has also been found.

All these phenomena produce an unsightly effect which it is very clearly desirable to avoid.

With the aim of lessening these phenomena, provision has been made in WO 97/16157 to combine, with a volatile solvent, a polymeric emulsifier of organosiloxane type having at least one hydrophilic radical and at least one lipophilic radical.

However, if it is desired to introduce pigments into these products, a problem of homogeneity of the pigments can be encountered.

In all cases, the compositions of the prior art could be improved regarding both stability and homogeneity of the dispersion of the pigments.

The aim of the present invention is to provide an anhydrous composition which can exhibit good stability, little transfer and very good dispersion of the pigments and thus improved cosmetic properties.

It has now been discovered, unexpectedly and surprisingly, that, with the use of a specific surfactant, it was possible to obtain anhydrous compositions having not only good stability over time but also with respect to temperature variations and furthermore exhibiting excellent cosmetic properties, in particular a homogeneous dispersion of the pigments.

The subject-matter of the present invention is therefore an anhydrous composition, in particular for cosmetic, dermatological, hygienic or pharmaceutical use, comprising at least one volatile solvent and at least one pigment, characterized in that it comprises at least one oxyalkylenated silicone substituted at the $\alpha$ and $\omega$ positions.

The invention also relates to a process for the non-therapeutic treatment of the skin and/or of the scalp, in particular a make-up process, which comprises applying, to the skin or mucous membranes and/or to the scalp, a composition as defined above.

The anhydrous composition according to the invention is preferably particularly stable.

The anhydrous composition according to the invention is preferably particularly homogeneous, making possible a uniform and homogeneous make-up.

Preferably, the anhydrous composition according to the invention additionally exhibits good resistance to transfer. Furthermore, when applied to the skin, it can exhibit the advantage of not migrating into the folds of the skin and/or the wrinkles of the face.

It has been found that the composition used according to the invention can be applied and spread easily in a homogeneous way without leaving a feeling of greasiness and can exhibit good cosmetic properties. The film obtained can also exhibit a light texture and remain comfortable to wear throughout the day.

Furthermore, the composition according to the invention can have good sensory qualities, in particular great ease of application, comfort, softness, good mattness and good covering power, uniformity and hold.

The compositions of the invention are anhydrous compositions. The term "anhydrous composition" is understood to mean a composition comprising less than 5% by weight of water with respect to the total weight of the composition, preferably from 1% to 2% of water, more preferably less than 1% of water. Most preferably still, the composition does not comprise water at all. The compositions of the invention are preferably devoid of polyvalent alcohols, that is to say of alcohols comprising at least two OH groups, such as propylene glycol, butylene glycol, glycerol or sorbitol.

In this application, silicone is understood to denote, in accordance with what is generally accepted, all organosilicon polymers or oligomers
- with linear or cyclic, branched or crosslinked structure,
- of variable molecular weight,
- obtained by polymerization and/or polycondensation of suitably functionalized silanes and
- essentially composed of a repetition of main units in which the silicon atoms are connected to one another via oxygen atoms (siloxane bond $\equiv$Si—O—Si$\equiv$), optionally substituted hydrocarbon-comprising radicals being directly bonded via a carbon atom to the said silicon atoms.

The most common optionally substituted hydrocarbon-comprising radicals are alkyl radicals, in particular $C_1$–$C_{10}$ alkyl radicals and especially methyl radicals, fluoroalkyl radicals or aryl radicals, in particular the phenyl radical.

Thus, the oxyalkylenated silicone substituted at the $\alpha$ and $\omega$ positions which can be used for the composition according to the invention is an organosilicon polymer as defined above, with a linear structure, substituted at the two ends of the main chain by oxyalkylene groups connected to the Si atoms via a hydrocarbon-comprising group. Preferably, the main chain does not comprise a pendant oxyalkylene group.

The oxyalkylenated silicone substituted at the $\alpha$ and $\omega$ positions preferably corresponds to the following general formula (I):

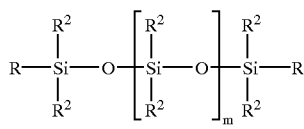  (I)

in which:

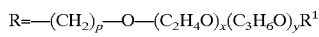

where:

$R^1$ represents H, $CH_3$ or $CH_2CH_3$, p is an integer ranging from 1 to 5, x varies from 1 to 100 and y varies from 0 to 50, it being possible for the $(C_2H_4O)$ and $(C_3H_6O)$ units to be randomly distributed or to be distributed by blocks, the $R^2$ radicals represent a $C_1$-$C_3$ alkyl radical or a phenyl radical, $5 \leq m \leq 300$.

The oxyalkylenated silicone substituted at the α and ω positions used according to the present invention preferably corresponds to the general formula (I) in which all the $R^2$ radicals are methyl radicals and:

ranges from 2 to 4, x ranges from 3 to 100, m ranges from 50 to 200.

More preferably, the average molecular weight of R ranges from 800 to 2600.

The ratio by weight of the $C_2H_4O$ units with respect to the $C_3H_6O$ units preferably ranges from 100:10 to 20:80.

This ratio is preferably approximately 42/58.

More preferably, $R^1$ is the methyl group.

In an even more preferable way, the composition according to the invention comprises the oxyalkylenated silicone substituted at the α and ω positions of following formula:

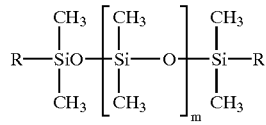

in which:

m=100, $R=(CH_2)_3$—O—$(C_2H_4O)_x(C_3H_6O)_y$—$CH_3$, where x ranges from 3 to 100 and y ranges from 1 to 50, the ratio by weight of the $C_2H_4O$ number to the $C_3H_6O$ number being approximately 42/58 and the average molecular weight of R ranging from 800 to 1500.

The oxyalkylenated silicone substituted at the α and ω positions as defined above is used according to the invention in a proportion ranging from 0.1 to 20%, preferably ranging from 0.1 to 10%, by weight with respect to the total weight of the composition.

Mention may in particular be made, among commercial products which can comprise all or part of the oxyalkylenated silicones and which can be used according to the invention as emulsifier, of those sold under the names of "Abil EM 97" by the Company Goldschmidt or of "KF 6009", "X22-4350", "X22-4349" or "KF 6008" by the Company Shin Etsu.

The compositions according to the invention comprise at least one pigment.

The pigments can be present in the composition at a content ranging from 0.1 to 20% by weight with respect to the total weight of the composition and preferably in a proportion of 2–15%. They can be white or coloured, inorganic and/or organic. Mention may be made, among inorganic pigments, of titanium, zirconium or cerium dioxides, as well as zinc, iron or chromium oxides, ferric blue or pearlescent agents, such as mica covered with titanium oxide, with iron oxide, with natural pigment or with bismuth oxychloride, as well as coloured titanium oxide-coated mica. Mention may be made, among organic pigments, of carbon black and barium, strontium, calcium or aluminium lakes. The pigments can also exhibit hydrophobic surfaces or can be treated so as to render their surfaces hydrophobic; this treatment can be carried out according to methods known to a person skilled in the art; the pigments can in particular be coated with silicone compounds, such as PDMSs, and/or with polymers, in particular polyethylenes, and/or amino acids.

Mention may in particular be made, among coated pigments, of the pigments sold under the name of "Covasil" by the Company Wacker (pigments with triisostearoyl titanate).

The pigments, thus coated, can be incorporated into the composition according to the invention in a proportion of between 0.1 and 15% by weight with respect to the total weight of the composition.

The composition according to the invention comprises at least one volatile solvent. The term "volatile solvent" is understood to mean a compound which evaporates at room temperature (T=25° C.). The volatile solvent preferably has a viscosity ranging from 0.5 to 25 centistokes at 25° C. The volatile solvents which can be used according to the present invention can, for example, be linear or cyclic silicones, that is to say linear or cyclic polydiorganosiloxanes, which are optionally functionalized, or hydrocarbon-comprising paraffins or their mixtures.

The optionally functionalized linear polydiorganosiloxanes which can be used according to the invention correspond to the following general formula:

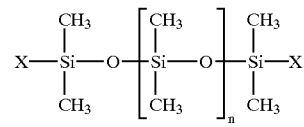

in which:

X is $CH_3$ or OH, and n is an integer ranging from 0 to 2000.

Mention will in particular be made, among these, of the products sold under the name of "AK" by the Company Wacker, "SF" by the Company General Electric and "Abil" by the Company Goldschmidt, such as the product "Abil 10".

Use may be made, as cyclic polydiorganosiloxanes according to the invention, alone or as a mixture, of the cyclomethicones of formula:

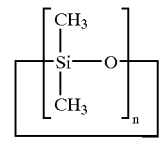

in which:

n is an integer from 3 to 8.

Mention will be made, among particularly preferred cyclomethicones, of cyclotetradimethylsiloxane (n=4), cyclopentadimethylsiloxane (n=5), and cyclohexadimethylsiloxane (n=6).

Use may in particular be made of the products sold under the names of "DC Fluid 244", "DC Fluid 245", "DC Fluid 344" and "DC Fluid 345" by the Company Dow Corning.

Other cyclomethicones which can be used according to the invention are those sold under the names of "Abil K4" by the Company Goldschmidt; under the names of "Silbione 70045 V2" and of "Silbione Oil 70045 V5" by the Company Rhone-Poulenc; and under the names of "volatile Silicone 7158" and of "Volatile Silicone 7207" by the Company Union Carbide.

The volatile solvents can also be paraffins with straight or branched hydrocarbon-comprising chains having from 8 to 40 carbon atoms, preferably from 10 to 20 carbon atoms. These solvents are, for example, decane, dodecane, tetradecane, tridecane or $C_8$–$C_{20}$ isoparaffins, such as, for example, those disclosed in U.S. Pat. No. 3,439,088 and U.S. Pat. No. 3,818,105. The preferred paraffins according to the present invention are, for example, those having a molecular weight ranging from 160 to 180. They also preferably have a boiling point ranging from 105 to 320° C. The paraffins again preferably have a viscosity of less than or equal to 20 cSt (centistokes) at 25° C. Such paraffins are sold, for example, by Exxon under the trade name "Isopars".

The volatile solvent used in the compositions according to the invention is generally present in the compositions of the invention at a content ranging from 0.5 to 80% by weight with respect to the total weight of the composition, preferably at a content ranging from 5 to 80%.

Use is preferably made of volatile silicone oils and more preferably of cyclomethicones.

The compositions according to the invention can also comprise non-volatile fatty substances.

Mention may be made, among non-volatile fatty substances, of non-volatile oils, pasty fatty substances, or vegetable, mineral, animal and/or synthetic gums and waxes, the synthetic gums and waxes comprising silicone fatty substances.

The compositions according to the invention can also comprise non-volatile oils. These oils preferably have a viscosity ranging from 0.5 to 1,000,000 centistokes, more preferably ranging from 25 to 600,000 centistokes, at 25° C. Examples of such oils are essential oils, esters, glycerol esters of fatty acids, fatty acids, fatty alcohols and their mixtures. Examples of esters which are suitable for the compositions according to the invention are acetylglycerides or octanoates, decanoates or ricinoleates of alcohols or of polyalcohols; castor oil, lanolin and its derivatives, palm oil, olive oil, soybean oil or cereal germ oils.

Examples of oils which are also suitable for the present invention are non-volatile paraffins, such as polyisobutene, mineral oils, polydecene, squalane or liquid petrolatum.

These oils are preferably present in the composition according to the invention at a content ranging from 0.1 to 80% by weight with respect to the total weight of the composition, more preferably from 0.1 to 50%.

The compositions according to the invention can also comprise waxes.

Mention may be made, as waxes which can be used in the invention, of waxes of animal origin, such as lanolin, beeswax, spermaceti or lanolin derivatives, such as lanolin alcohols, hydrogenated, hydroxylated or acetylated lanolin, lanolin fatty acids and acetylated lanolin alcohol; waxes of vegetable origin, such as carnauba, candelilla, kapok, ouricury, rice, hydrogenated jojoba, esparto or japan wax or cork fibre or sugar cane waxes or cocoa butter; mineral waxes, for example paraffin, montan, lignite or petrolatum waxes or microcrystalline waxes, ceresin or ozokerite; or synthetic waxes, such as polyethylene waxes, waxes obtained by the Fischer-Tropsch synthesis and linear esters resulting from the reaction of a saturated $C_{10}$ to $C_{40}$ carboxylic acid and of a saturated $C_{10}$ to $C_{40}$ alcohol, such as myristyl myristate. Use may also be made of cetyl alcohol, stearyl alcohol, calcium lanolates or stearates, castor oil, palm oil, coconut oil, sunflower oil or hydrogenated coconut oil.

The waxes can be present in the compositions according to the invention generally at a content which can range up to 40% by weight with respect to the total weight of the composition and more preferably up to 20%.

The pasty fatty compounds can be defined using at least one of the following physicochemical properties:

a viscosity of 0.1 to 40 Pa·s (1 to 400 poises), preferably 0.5 to 25 Pa·s, measured at 40° C. with a Contraves TV rotary viscometer equipped with an MS-r3 or MS-r4 rotor at a frequency of 60 Hz, a melting point of 25–70° C., preferably 25–55° C.

The compositions of the invention can also comprise alkyl, alkoxy or phenyl dimethicones, such as, for example, the product sold under the name of "Abil Wax 2440" by the Company Goldschmidt.

The compositions according to the invention can also comprise silicone resins comprising a combination of the $R_3SiO_{1/2}$, $R_2SiO_{2/2}$, $RSiO_{3/2}$ and $SiO_{4/2}$ units, R representing an alkyl group having from 1 to 6 carbon atoms or a phenyl group.

Mention may be made, among silicone fatty substances, of poly($C_1$–$C_{20}$)alkylsiloxanes, phenylated silicone oils, such as, for example, the phenyl trimethicone sold under the trade name "Abil AV 1000" by Goldschmidt, and silicone gums and silicone waxes.

The silicone gums can correspond to the formula:

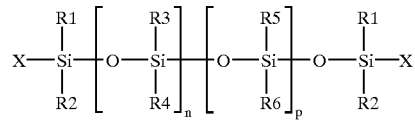

in which:

R1, R2, R5 and R6 are, together or separately, an alkyl radical having 1 to 6 carbon atoms, R3 and R4 are, together or separately, an alkyl radical having from 1 to 6 carbon atoms or an aryl radical and in particular a phenyl radical, X is an alkyl radical having from 1 to 6 carbon atoms, a hydroxyl radical or a vinyl radical, n and p being chosen so as to confer, on the silicone gum, a viscosity greater than 100,000 mPa·s, preferably greater than 500,000 mPa·s.

Generally, n and p can take values from 0 to 5000, preferably from 0 to 3000.

Mention may be made, as silicone gum which can be used according to the invention, of those for which:

the R1 to R6 and X substituents represent a methyl group, p=0 and n=2700, such as that sold under the name SE30 by the company General Electric, the R1 to R6 and X substituents represent a methyl group, p=0 and n=2300, such as that sold under the name AK 500000 by the company Wacker, the R1 to R6 substituents represent a methyl group, the X substituent represents a hydroxyl group, p=0 and n=2700, as a 13% solution in cyclopentasiloxane, such as that sold under the name Q2-1401 by the company Dow Corning, the R1 to R6 substituents represent a methyl group, the X substituent represents a hydroxyl group, p=0 and n=2700, as a 13% solution in polydimethylsiloxane, such as that sold under the name Q2-1403 by the company Dow Corning, the R1, R2, R5, R6 and X substituents represent a methyl group and the R3 and R4 substituents represent a phenyl group, such that the molecular weight of the compound is 600,000, such as that sold under the names "761" or "Mirasil C-DPDM" by the company Rhône-Poulenc.

These fatty substances can in particular be chosen in a way varied by a person skilled in the art in order to prepare a composition having the desired properties, for example of consistency or of texture. They are preferably used at a content of less than or equal to 7% by weight with respect to the total weight of the emulsion, in order to retain the advantageous properties of the emulsion used according to the invention.

Mention may be made, among other fat-soluble adjuvants which can be incorporated in the composition, of lipophilic U.V. screening agents, lipophilic vitamins, antioxidants and fragrances, or ceramides.

The composition according to the invention can also comprise a particulate phase which can comprise, in addition to the pigments already mentioned above, pearlescent agents and/or fillers commonly used in cosmetic compositions.

The fillers, which can be present in the composition in a proportion of 0–20% by weight with respect to the total weight of the composition, preferably 0–10%, can be inorganic or synthetic, lamellar or non-lamellar. Mention may be made of talc, mica, silica, kaolin, teflon, starch, natural mother-of-pearl, boron nitride, microspheres, such as Expancel (Nobel Industrie), or microsponges, such as polytrap (Dow Corning). Use is preferably made of spherical fillers with a size of less than 25 $\mu$m, such as polyethylene powders, nylon powders, silicone resin microbeads (Tospearls from Toshiba) or silica microspheres, it being possible for these fillers to contribute to improving the non-transfer properties of the compositions of the invention.

The composition according to the invention can additionally comprise a cosmetically, pharmaceutically or hygienically acceptable medium. It can then comprise any additive commonly used in the cosmetics, pharmaceutical or hygiene field, such as antioxidants, colorants, fragrances, essential oils, preservatives, cosmetic active principles, moisturizers, vitamins, sphingolipids or fat-soluble polymers, in particular hydrocarbon-comprising polymers, such as polybutene, polyalkylenes, polyacrylates and silicone polymers compatible with fatty substances.

These additives can be present in the composition in a proportion of 0–10% by weight.

Of course, a person skilled in the art will take care to choose this or these optional additional compounds and/or their amount so that the advantageous properties of the composition according to the invention are not, or not substantially, detrimentally affected by the envisaged addition.

The compositions according to the invention can be provided in the form of a cosmetic product and in particular in the form of a care product for the body and/or the face and/or the scalp or alternatively of a make-up product, in particular a foundation, a face powder, an eyeshadow, an eyeliner, a mascara or a lipstick.

They can also be provided in a non-coloured form, optionally comprising cosmetic active principles.

The compositions according to the invention can be provided in the form of a fluid gel or of a stick.

The compositions according to the invention are preferably provided in a fluid form and have a Brookfield viscosity, measured on the LVDV model, with a 3 spindle, at a speed of 60 rev/min and at approximately 25° C., ranging from 8 poises to 50 poises.

The invention also relates to the use of an oxyalkylenated silicone substituted at the $\alpha$ and $\omega$ positions as defined above in an anhydrous composition comprising pigments and a volatile solvent with the aim of improving the dispersion of the said pigments in the said composition.

The invention also relates to the use of an oxyalkylenated silicone substituted at the $\alpha$ and $\omega$ positions as defined above in an anhydrous composition comprising pigments and a volatile solvent with the aim of improving the homogeneity of the said composition.

COMPARATIVE EXAMPLE

The Inventors have prepared the following anhydrous compositions:

Composition A (Conforms to the Invention):
cyclomethicone 97.5 g
mixture of oxyethylenated-oxypropylenated silicone substituted at the $\alpha$ and $\omega$ positions and of cyclomethicone (85/15), sold under the trade name "Abil EM 97" by the Company Goldschmidt 2.5 g
pigments 50 g Composition B (Comparative):
cyclomethicone 97.5 g
silicone comprising pendant alkyl, oxyethylene and oxypropylene groups in a polyglyceryl-4 isostearate and hexyl laurate mixture, sold under the trade name "Abil WE 09" by the company Goldschmidt 2.5 g
pigments 50 g The Inventors subsequently measured the viscosities at time t=3 minutes of the compositions A and B. These viscosities were measured with a Brookfield, model LVDV, with a 3 spindle, at a speed of 60 rev/min and at approximately 25° C. The results are combined in the following table:

| Composition | Brookfield viscosity in poises |
| --- | --- |
| A (conforms to the invention) | 8.8 |
| B (comparative) | 14 |

Thus, the anhydrous composition A, for the same level of pigment, is much more fluid than the composition B. The composition A exhibits a more homogeneous texture than the composition B. The pigments are better dispersed in the composition A according to the invention than in the composition B.

What is claimed is:

1. An anhydrous composition comprising at least one volatile solvent, at least one pigment, and at least one oxyalkylenated silicon substituted at the $\alpha$ and $\omega$ positions, wherein said anhydrous composition contains less than 1% by weight of water with respect to the total weight of the composition, and wherein said at least one oxyalkylenated silicone substituted at the $\alpha$ and $\omega$ positions is chosen from compounds of the formula (I):

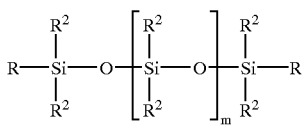

(I)

in which: $R=-(CH_2)_p-O-(C_2H_4O)_x(C_3H_6O)_yR^1$
where:
$R^1$ is chosen from H, $CH_3$ and $CH_2CH_3$,
p is an integer ranging from 2 to 4,
x ranges from 3 to 100,
y ranges from 0 to 50,
m ranges from 50 to 200,
it being possible for the $(C_2H_4O)$ and $(C_3H_6O)$ units to be randomyl distributed or to be distributed by blocks, and
the $R^2$ radicals are chosen from methyl radicals.

2. The composition according to claim 1, wherein said anhydrous composition contains no water.

3. The composition according to claim 1, wherein the average molecular weight of R ranges from 800 to 2600.

4. The composition according to claim 1, wherein the ratio by weight of the $C_2H_4O$ units with respect to the $C_3H_6O$ unit ranges from 100:10 to 20:80.

5. The composition according to claim 4, wherein the ratio is approximately 42/58.

6. The composition according to claim 1, wherein said at least one oxyalkylenated silicone is chosen from compounds of the formula:

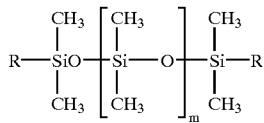

in which:
m=100,
$R=-(CH_2)_3-O-(C_2H_4O)_x(C_3H_6O)_y-CH_3$, where x ranges from 3 to 100 and y ranges from 1 to 50, the ratio by weight of the $C_2H_4O$ number to the $C_3H_6O$ number being approximately 42/58 and the average molecular weight of R ranging from 800 to 1500.

7. The composition according to claim 1, wherein said at least one oxyalkylenated silicone is present in the composition in a proportion ranging from 0.1 to 20% by weight with respect to the total weight of the composition.

8. The composition according to claim 7, wherein said at least one oxyalkylenated silicone is present in a proportion ranging from 0.1 to 10% by weight with respect to the total weight of the composition.

9. The composition according to claim 1, wherein said at least one pigment is chosen from titanium, zirconium and cerium dioxides, zinc, iron and chromium oxides, ferric blue, pearlescent agents, carbon black, barium, strontium, calcium, aluminium lakes, pigments coated with silicone compounds, pigments coated with polymers, pigments coated with amino acids, and pigments coated with a mixture chosen from silicone compounds, polymers, and amino acids.

10. The composition according to claim 9, wherein said pearlescent agents are chosen from mica covered with titanium oxide, mica covered with iron oxide, mica covered with natural pigment, and mica covered with bismuth oxychloride.

11. The composition according to claim 10, wherein said titanium oxide is colored.

12. The composition according to claim 9, wherein said silicone compounds are PDMSs.

13. The composition according to claim 9, wherein said polymers are polyethylenes.

14. The composition according to claim 1, wherein said at least one pigment is present in the composition at a content ranging from 0.1 to 20% by weight with respect to the total weight of the composition.

15. The composition according to claim 14, wherein said content ranges from 2 to 15% by weight with respect to the total weight of the composition.

16. The composition according to claim 1, wherein said at least one volatile solvent has a viscosity ranging from 0.5 to 25 centistokes at 25° C.

17. The composition according to claim 1, wherein said at least one volatile solvent is chosen from linear and cyclic polydiorganosiloxanes, which are optionally functionalized, and hydrocarbon-comprising paraffins.

18. The composition according to claim 1, wherein said at least one volatile solvent is chosen from decane, dodecane, tetradecane, tridecane and $C_8$–$C_{20}$ isoparaffins.

19. The composition according to claim 1, wherein said at least one volatile solvent is a cyclomethicone.

20. The composition according to claim 1, wherein said at least one volatile solvent is present in the composition in a proportion ranging from 0.5% to 80% by weight with respect to the total weight of the composition.

21. The composition according to claim 20, wherein said content ranges from 5 to 80% by weight with respect to the total weight of the composition.

22. The composition according to claim 1, wherein said composition further comprises a wax chosen from waxes of animal origin, waxes of vegetable origin, mineral waxes, synthetic waxes, cetyl alcohol, stearyl alcohol, calcium lanolates and stearates, castor oil, palm oil, coconut oil, sunflower oil and hydrogenated coconut oil.

23. The composition according to claim 22, wherein said waxes of animal origin are chosen from lanolin, beeswax, spermaceti and lanolin derivatives.

24. The composition according to claim 23, wherein said lanolin derivatives are chosen from lanolin alcohols, hydrogenated, hydroxylated, and acetylated lanolins, lanolin fatty acids and acetylated lanolin alcohol.

25. The composition according to claim 22, wherein said waxes of vegetable origin are chosen carnauba, candelilla, kapok, ouricury, rice, hydrogenated jojoba, esparto, japan wax, cork fibre, sugar cane waxes and cocoa butter.

26. The composition according to claim 22, wherein said mineral waxes are chosen from paraffin, montan, lignite, petrolatum waxes, microcrystalline waxes, ceresin and ozokerite.

27. The composition according to claim 22, wherein said synthetic waxes are chosen from polyethylene waxes, waxes obtained by the Fischer-Tropsch synthesis and linear esters resulting from the reaction of a saturated $C_{10}$ to $C_{40}$ carboxylic acid and of a saturated $C_{10}$ to $C_{40}$ alcohol.

28. The composition according to claim 27, wherein said linear esters are myristyl myristate.

29. The composition according to claim 1, wherein said composition further comprises a filler chosen from talc, mica, silica, kaolin, teflon, starch, natural mother-of-pearl, boron nitride, microspheres, microsponges, polyethylene powders, nylon powders, silicone resin microbeads and silica microspheres.

30. The composition according to claim 1, wherein said composition is a cosmetic composition, a dermatological composition, a hygienic composition or a pharmaceutical composition.

31. The composition according to claim 1, wherein said composition is in the form of a body care product, a face care product, a scalp care product, a combination thereof, or a make-up product.

32. The composition according to claim 31, wherein said make-up product is in the form of a foundation, a face powder, an eyeshadow, an eyeliner, a mascara or a lipstick.

33. The composition according to claim 1, wherein said composition is in the form of a fluid gel or a stick.

34. An anhydrous composition comprising at least one volatile solvent, at least one pigment, and at least one oxyalkylenated silicon substituted at the α and ω positions, wherein said anhydrous composition contains no polyhydric alcohols, and wherein said at least one oxyalkylenated silicone substituted at the α and ω positions is chosen from compounds of the formula (I):

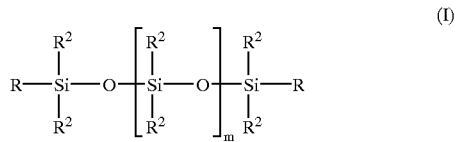
(I)

in which: R—$(CH_2)_p$—O—$(C_2H_4O)_x(C_3H_6O)_y R^1$
where:
$R^1$ is chosen from H, $CH_3$ and $CH_2CH_3$,
p is an integer ranging from 2 to 4,
x ranges from 3 to 100,
y ranges from 0 to 50,
m ranges from 50 to 200,
it being possible for the $(C_2H_4O)$ and $(C_3H_6O)$ units to be randomly distributed or to be distributed by blocks, and
the $R^2$ radicals are chosen from methyl radicals.

35. The composition according to claim 34, wherein the average molecular weight of R ranges from 800 to 2600.

36. The composition according to claim 34, wherein the ratio by weight of the $C_2H_4O$ units with respect to the $C_3H_6O$ unit ranges from 100:10 to 20:80.

37. The composition according to claim 36, wherein the ratio is approximately 42/58.

38. The composition according to claim 34, wherein said at least one oxyalkylenated silicone is chosen from compounds of the formula:

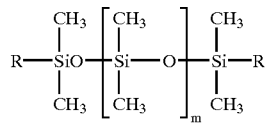

in which:
m=100,
R=—$(CH_2)_3$—O—$(C_2H_4O)_x(C_3H_6O)_y$—$CH_3$, where x ranges from 3 to 100 and y ranges from 1 to 50, the ratio by weight of the $C_2H_4O$ number to the $C_3H_6O$ number being approximately 42/58 and the average molecular weight of R ranging from 800 to 1500.

39. The composition according to claim 34, wherein said at least one oxyalkylenated silicone is present in the composition in a proportion ranging from 0.1 to 20% by weight with respect to the total weight of the composition.

40. The composition according to claim 39, wherein said at least one oxyalkylenated silicone is present in a proportion ranging from 0.1 to 10% by weight with respect to the total weight of the composition.

41. The composition according to claim 34, wherein said at least one pigment is chosen from titanium, zirconium and cerium dioxides, zinc, iron and chromium oxides, ferric blue, pearlescent agents, carbon black, barium, strontium, calcium, aluminium lakes, pigments coated with silicone compounds, pigments coated with polymers, pigments coated with amino acids, and pigments coated with a mixture chosen from silicone compounds, polymers, and amino acids.

42. The composition according to claim 41, wherein said pearlescent agents are chosen from mica covered with titanium oxide, mica covered with iron oxide, mica covered with natural pigment, and mica covered with bismuth oxychloride.

43. The composition according to claim 42, wherein said titanium oxide is colored.

44. The composition according to claim 41, wherein said silicone compounds are PDMSs.

45. The composition according to claim 41, wherein said polymers are polyethylenes.

46. The composition according to claim 34, wherein said at least one pigment is present in the composition at a content ranging from 0.1 to 20% by weight with respect to the total weight of the composition.

47. The composition according to claim 34, wherein said at least one volatile solvent has a viscosity ranging from 0.5 to 25 centistokes at 25° C.

48. The composition according to claim 34, wherein said at least one volatile solvent is chosen from linear and cyclic polydiorganosiloxanes, which are optionally functionalized, and hydrocarbon-comprising paraffins.

49. The composition according to claim 34, wherein said at least one volatile solvent is chosen from decane, dodecane, tetradecane, tridecane and $C_8$–$C_{20}$ isoparaffins.

50. The composition according to claim 34, wherein said at least one volatile solvent is a cyclomethicone.

51. The composition according to claim 34, wherein said at least one volatile solvent is present in the composition in a proportion ranging from 0.5% to 80% by weight with respect to the total weight of the composition.

52. The composition according to claim 51, wherein said content ranges from 5 to 80% by weight with respect to the total weight of the composition.

53. The composition according to claim 34, wherein said composition further comprises a wax chosen from waxes of animal origin, waxes of vegetable origin, mineral waxes, synthetic waxes, cetyl alcohol, stearyl alcohol, calcium lanolates or stearates, castor oil, palm oil, coconut oil, sunflower oil and hydrogenated coconut oil.

54. The composition according to claim 53, wherein said waxes of animal orign are chosen from lanolin, beeswax, spermaceti and lanolin derivatives.

55. The composition according to claim 54, wherein said lanolin derivatives are chosen from lanolin alcohols, hydrogenated, hydroxylated, and acetylated lanolins, lanolin fatty acids and acetylated lanolin alcohol.

56. The composition according to claim 53, wherein said waxes of vegetable origin are chosen carnauba, candelilla, kapok, ouricury, rice, hydrogenated jojoba, esparto, japan wax, cork fibre, sugar cane waxes and cocoa butter.

57. The composition according to claim 53, wherein said mineral waxes are chosen from paraffin, montan, lignite, petrolatum waxes, microcrystalline waxes, ceresin and ozokerite.

58. The composition according to claim 53, wherein said synthetic waxes are chosen from polyethylene waxes, waxes obtained by the Fischer-Tropsch synthesis and linear esters resulting from the reaction of a saturated $C_{10}$ to $C_{40}$ carboxylic acid and of a saturated $C_{10}$ to $C_{40}$ alcohol.

59. The composition according to claim 58, wherein said linear esters are myristyl myristate.

60. The composition according to claim 34, wherein said composition further comprises a filler chosen from talc, mica, silica, kaolin, teflon, starch, natural mother-of-pearl, boron nitride, microspheres, microsponges, polyethylene powders, nylon powders, silicone resin microbeads and silica microspheres.

61. The composition according to claim 34, wherein said composition is a cosmetic composition, a dermatological composition, a hygienic composition or a pharmaceutical composition.

62. The composition according to claim 34, wherein said composition is in the form of a body care product, a face care product, a scalp care product, a combination thereof, or a make-up product.

63. The composition according to claim 34, wherein said make-up product is in the form of a foundation, a face powder, an eyeshadow, an eyeliner, a mascara or a lipstick.

64. The composition according to claim 34, wherein said composition is in the form of a fluid gel or a stick.

65. A method for the non-therapeutic treatment of skin, mucous membrane, scalp, wherein said process comprises applying to the skin, the mucous membrane or the scalp, an anhydrous composition comprising at least one volatile solvent, at least one pigment, and at least one oxyalkylenated silicone substituted at the α and ω positions, wherein said anhydrous composition contains less than 1% by weight of water with respect to the total weight of the composition, and wherein said at least one oxyalkylenated silicone substituted at the α and ω positions is chosen from compounds of the formula (I):

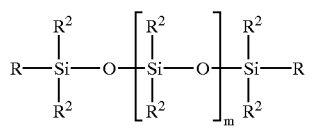

in which: $R = -(CH_2)_p-O-(C_2H_4O)_x(C_3H_6O)_yR^1$ where:

$R^1$ is chosen from H, $CH_3$ and $CH_2CH_3$, p is an integer ranging from 2 to 4, x ranges from 3 to 100, y ranges from 0 to 50, m ranges from 50 to 200, it being possible for the $(C_2H_4O)$ and $(C_3H_6O)$ units to be randomly distributed or to be distributed by blocks, and the $R^2$ radicals are chosen from methyl radicals.

66. A method according to claim 65, wherein said process is a make-up process.

67. A method for the non-therapeutic treatment of the skin or of the scalp or both, wherein said process comprises applying to the skin, the mucous membrane or the scalp, an anhydrous composition comprising at least one volatile solvent, at least one pigment, and at least one oxyalkylenated silicone substituted at the α and ω positions, wherein said anhydrous composition contains no polyhydric alcohols, and wherein said at least one oxyalkylenated silicone substituted at the α and ω positions is chosen from compounds of the formula (I):

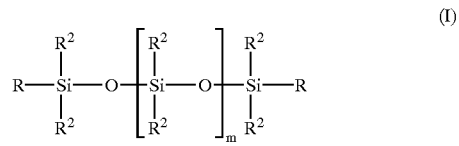

in which: $R = -(CH_2)_p-O-(C_2H_4O)_x(C_3H_6O)_yR^1$ where:

$R^1$ is chosen from H, $CH_3$ and $CH_2CH_3$, p is an integer ranging from 2 to 4, x ranges from 3 to 100, y ranges from 0 to 50, m ranges from 50 to 200, it being possible for the $(C_2H_4O)$ and $(C_3H_6O)$ units to be randomly distributed or to be distributed by blocks, and the $R^2$ radicals are chosen from methyl radicals.

68. A method according to claim 67, wherein said process is a make-up process.

* * * * *

UNITED STATES PATENT AND TRADEMARK OFFICE
CERTIFICATE OF CORRECTION

PATENT NO. : 6,589,538 B1
DATED : July 8, 2003
INVENTOR(S) : Patricia Lemann et al.

It is certified that error appears in the above-identified patent and that said Letters Patent is hereby corrected as shown below:

Column 9,
Line 17, "randomly" should read -- randomly --.

Column 10,
Line 45, "chosen carnauba," should read -- chosen from carnauba, --.

Column 11,
Line 26, "in which: R" should read -- in which R= --.

Column 12,
Line 59, "chosen carnauba," should read -- chosen from carnauba, --.

Signed and Sealed this

Twenty-first Day of October, 2003

JAMES E. ROGAN
*Director of the United States Patent and Trademark Office*